United States Patent
Dutheil et al.

(10) Patent No.: US 9,861,095 B2
(45) Date of Patent: Jan. 9, 2018

(54) **USE OF EXTRACELLULAR HEMOGLOBIN OBTAINED FROM THE MARINE WORM, *ARENICOLA MARINA*, FOR THE PRESERVATION OF ORGANS, TISSUES, CELLS**

(75) Inventors: Delphine Dutheil, Saint Julien l'ars (FR); Morgane Rousselot, Saint Pol de Leon (FR); Thierry Hauet, Miganloux Beauvoir (FR); Franck Zal, Ploujean-Morlaix (FR)

(73) Assignee: HEMARINA, Morlaix (FR)

( * ) Notice: Subject to any disclaimer, the term of this patent is extended or adjusted under 35 U.S.C. 154(b) by 537 days.

(21) Appl. No.: 14/119,712

(22) PCT Filed: May 30, 2012

(86) PCT No.: PCT/FR2012/051206
§ 371 (c)(1),
(2), (4) Date: Nov. 22, 2013

(87) PCT Pub. No.: WO2013/001196
PCT Pub. Date: Jan. 3, 2013

(65) Prior Publication Data
US 2014/0113274 A1    Apr. 24, 2014

(30) Foreign Application Priority Data
May 31, 2011    (FR) .................... 11 54778

(51) Int. Cl.
*A01N 1/02* (2006.01)
*A61K 38/42* (2006.01)
*C12N 5/00* (2006.01)

(52) U.S. Cl.
CPC ............ *A01N 1/0226* (2013.01); *A61K 38/42* (2013.01); *C12N 5/0037* (2013.01)

(58) Field of Classification Search
CPC .................................................. A01N 1/0226
USPC ......................................................... 435/1.1
See application file for complete search history.

(56) References Cited

U.S. PATENT DOCUMENTS

| | | | |
|---|---|---|---|
| 5,556,842 A | 9/1996 | Shimizu et al. | |
| 8,846,306 B2 * | 9/2014 | Zal | A01N 1/02 435/1.1 |

FOREIGN PATENT DOCUMENTS

| | | | | |
|---|---|---|---|---|
| FR | 2 919 785 A1 | 2/2009 | | |
| FR | 2919785 A1 * | 2/2009 | ............... | A01N 1/02 |
| FR | WO 2010128159 A1 * | 11/2010 | ........... | A01N 1/0226 |
| JP | H06192001 A | 7/1994 | | |
| WO | WO 2007/111495 A1 | 10/2007 | | |
| WO | WO 2010128159 A1 * | 11/2010 | ........... | A01N 1/0226 |

OTHER PUBLICATIONS

Weber, Roy. On the Variation in Oxygen-Binding Properties in Hemoglobins of Lugworms. Fifth EURoPEAN Marine Biology Symposium.*
Rousselot et al., "*Arenicola marina* Extracellular Hemoglogin: A New Promising Blood Substitute", Biotechnology Journal, vol. 1, No. 3, pp. 333-345 (Jan. 1, 2006).
Scheule et al., "Emergency Donor Heart Protection: Application of the Port Access Catheter Technique Using a Pig Heart Transplantation Model", Transplantation, vol. 77, No. 8, pp. 1166-1171 (Jan. 1, 2004).
Tariq Hafez et al., "Chapter 9—Organ Preservation for Transplantation", in: Baust et al, "Advances in Biopreservation", CRC Press pp. 197-270, (2006).
International Search Report corresponding to International Patent Application No. PCT/FR2012/051206 dated Nov. 10, 2012.
Written Opinion corresponding to International Patent Application No. PCT/FR2012/051206 dated Nov. 10, 2012.

* cited by examiner

*Primary Examiner* — Scott Long
*Assistant Examiner* — Nghi Nguyen
(74) *Attorney, Agent, or Firm* — McDonnell Boehnen Hulbert & Berghoff LLP

(57) ABSTRACT

Disclosed is a method for preserving an organ in a donation after brain death donor or a donation after cardiac death donor comprising administering to the donor a composition comprising at least one globin, one globin protomer or one extracellular hemoglobin of Annelida, a stabilizing solution and/or a solution for conserving organs, said composition having a temperature of between 0° C. and 37° C. Also disclosed is a method for conserving an organ in situ in a donation after brain death donor or a donation after cardiac death donor using normothermic ECMO or double-balloon triple-lumen catheter techniques or any other similar technique.

9 Claims, No Drawings

USE OF EXTRACELLULAR HEMOGLOBIN OBTAINED FROM THE MARINE WORM, *ARENICOLA MARINA*, FOR THE PRESERVATION OF ORGANS, TISSUES, CELLS

CROSS-REFERENCE TO RELATED APPLICATIONS

This application is a U.S. national phase of International Application No. PCT/FR2012/051206, filed May 30, 2012, the disclosure of which is hereby incorporated by reference in its entirety.

BACKGROUND OF THE INVENTION

Field of the Invention

The present invention relates to the use of a composition comprising at least one globin, one globin protomer or one extracellular hemoglobin of annelids, a stabilizing solution and/or a clinically used organ preservation solution, said composition having a temperature of between 0° C. and 37° C., for preserving at least one organ in situ in a donation after brain death donor or a donation after cardiac death donor.

Description of the Related Art

Organ donation is the harvesting of organs from a human body, called donor, for the purpose of treating a patient, called recipient, whose organs are seriously damaged.

One of the difficulties of this donation remains the organ preservation time. Indeed, in normothermia (37° C.), before and/or after harvesting from the donor, an organ undergoes a period of warm ischemia, i.e. a period where the organ is no longer perfused by the donor's blood, and is not yet refrigerated. It deteriorates rapidly and is no longer supplied with oxygen. The acceptable time for ensuring the subsequent resumption of function of the transplant organ varies from one organ to another, when said organ is preserved in hypothermia (i.e. at around 4° C.). For example, it is approximately 4 to 6 hours for a heart or a lung, 8 to 12 hours for a liver, 24 to 48 hours for a kidney and 8 to 10 hours for a pancreas or an intestine. The transplant must therefore be carried out within a well-defined period, in order to ensure that the organ functionality is maintained.

Moreover, hypothermia is the essential component of storage. As soon as it is removed, the transplant organ is cooled, in order to rapidly bring its temperature down from 37° C. to 4° C.; for this, the organ is rinsed with a preserving solution via the vessels and then simply immersed in this preserving solution kept at low temperature by crushed ice according to guaranteed aseptic conditions. The decrease in the temperature of the tissues leads to a decrease in cell metabolism, i.e. a slowing down of the catalytic enzymatic activity required for cell viability, without however stopping it (Belzer F. O., Southard J. H. Principles of solid-organ preservation by cold storage. Transplantation 1988; 45(4): 673-676). The transplant organ placed at 4° C. experiences a decrease in its metabolism of approximately 85%. Hypothermia thus makes it possible to combat the harmful effects of oxygen starvation and nutrient starvation induced by the arrest of blood circulation and defers cell death, responsible for tissue necrosis.

In the face of shortages of donations, preservation of the transplant organ and oxygenation thereof, over a longer period of time, are essential preoccupations; this allows the quality of the organ to be maintained, prolonged survival of the organ, and thus a successful transplant. Indeed, even though the metabolism of a transplant organ preserved at 4° C. is reduced, it still needs oxygen, like all aerobic tissues.

In addition, the majority of blood substitutes available today, such as perfluorocarbons (PFCs), HBOCs or human blood, are capable of oxygenating organs, but cannot be used at just any temperature. In particular, they are not functional or stable at 4° C. Moreover, PFCs are not oxygen transporters, but solutes capable of dissolving a large amount of oxygen according to the partial oxygen pressure. They cannot therefore be used simply, and can create oxidative stress problems.

SUMMARY OF INVENTION

Surprisingly, the inventors have now discovered that the administration, preferably by intracorporeal injection, of a specific composition, said composition having a temperature of between 0° C. and 37° C., in a donation after brain death donor or a donation after cardiac death donor, makes it possible to preserve and oxygenate said donor's organs under optimum conditions, in order to maintain their functions before they are harvested from said donor. The specific composition comprises an extracellular hemoglobin of annelids, a stabilizing solution and/or an organ preservation solution. The in situ administration of said composition makes it possible to maintain the functions of the organs under optimum conditions before they are harvested, and to cool said organs or to keep them at any temperature between 0 and 37° C., preferably in normothermia. The composition according to the invention, which contains an oxygen transporter, also makes it possible to efficiently oxygenate the organs in situ in the donor and to ensure their quality. Finally, the composition according to the invention is stable and functional both at 4° C. and at 37° C.

DETAILED DESCRIPTION OF THE INVENTION

The subject of the present invention is therefore the use of a composition comprising at least one globin, one globin protomer or one extracellular hemoglobin of annelids, a stabilizing solution and/or an organ preservation solution, said composition having a temperature of between 0° C. and 37° C., for preserving an organ in a donation after brain death donor or a donation after cardiac death donor. The preservation of the organ is therefore carried out directly in situ in the deceased donor. The composition according to the invention can be directly perfused in the donor awaiting harvesting of the various transplant organs (heart, lung, liver, kidneys, pancreas, intestine, cornea, etc.).

The subject of the invention is also the use of a composition comprising at least one globin, one globin protomer or one extracellular hemoglobin of annelids, a stabilizing solution and/or an organ preservation solution, said composition having a temperature of between 0° C. and 37° C., for preparing a pharmaceutical composition for preserving at least one organ in a donation after brain death donor or a donation after cardiac death donor. The subject of the present invention is also a composition comprising at least one globin, one globin protomer or one extracellular hemoglobin of annelids, a stabilizing solution and/or an organ preservation solution, said composition having a temperature of between 0° C. and 37° C., for use thereof for preserving at least one organ in a donation after brain death donor or a donation after cardiac death donor.

The subject of the present invention is also the use of an aqueous solution comprising sodium chloride, calcium chloride, magnesium chloride, potassium chloride, sodium gluconate and sodium acetate, and optionally one or more antioxidants, said aqueous solution having a pH of between 6.5 and 7.6, preferably equal to 7.1±0.5, preferably of approximately 7.35, for preserving at least one organ in situ in a donation after brain death donor or a donation after cardiac death donor. This aqueous solution can be combined with an organ preservation solution, i.e. it can be mixed with an organ preservation solution. Preferentially, said aqueous solution comprises 90 mM of NaCl, 23 mM of Na gluconate, 2.5 mM of $CaCl_2$, 27 mM of Na acetate, 1.5 mM of $MgCl_2$, 5 mM of KCl, and has a pH of 7.1±0.5, and optionally between 0 and 100 mM of antioxidant of ascorbic acid and/or reduced glutathione type. Said solution preferably has an osmolarity of between 300 and 350, and preferentially of 302 mOsmol/l.

According to the invention, the organ preservation is carried out directly in the donor post-mortem. The deceased donor may be in a state of brain death or in cardiac arrest. In the latter case, reference is made to non-heart-beating organ procurement.

Brain death, also known as irreversible coma or stage IV coma, is defined as the complete and definitive irreversible ceasing of brain activity, even though blood circulation persists. A donor is in a state of brain death, or encephalic death, when the encephalon is irreversibly destroyed, despite the temporary persistence of hemodynamic activity and of vascularization of the organs.

A donor is in cardiac arrest if this cardiac arrest is irreversible after resuscitation measures have been ceased. The period of time after which asystole is considered to be irreversible is about one minute, after resuscitation measures have been ceased. However, the recommendations require a period of more than 5 minutes.

The composition according to the invention comprises:
  at least one globin, one globin protomer or one extracellular hemoglobin of annelids, and
  a stabilizing solution and/or an organ preservation solution.

The composition according to the invention may thus comprise either at least one globin, one globin protomer or one extracellular hemoglobin of annelids, and a stabilizing solution; or at least one globin, one globin protomer or one extracellular hemoglobin of annelids, and an organ preservation solution; or at least one globin, one globin protomer or one extracellular hemoglobin of annelids, a stabilizing solution and an organ preservation solution.

The composition according to the invention therefore comprises at least one compound chosen from extracellular hemoglobin of annelids, globin protomers thereof and globins thereof.

The extracellular hemoglobin of annelids is present in the three classes of annelids: the polychaetes, the oligochaetes and the achaetes. Reference is made to extracellular hemoglobin because it is naturally not contained in a cell, and can therefore circulate freely in the blood stream without chemical modification to stabilize it or make it functional.

The extracellular hemoglobin of annelids is a giant biopolymer with a molecular weight of between 2000 and 4000 kDa, consisting of approximately 200 polypeptide chains of between 4 and 12 different types which are generally grouped into two categories.

The first category, with 144 to 192 components, groups together the "functional" polypeptide chains which bear an active site of heme type, and are capable of reversibly binding oxygen; these are chains of globin type, the weights of which are between 15 and 18 kDa and which are very similar to the α- and β-type chains of vertebrates.

The second category, with 36 to 42 components, groups together the "structural" or "linker" polypeptide chains which have few or no active sites but enable the assembly of the subunits called one-twelfth subunits or protomers.

Each hemoglobin molecule consists of two superposed hexagons which have been named hexagonal bilayer, and each hexagon is itself formed by the assembly of six subunits (or "one-twelfth subunits" or "protomers") in the form of a drop of water. The native molecule is made up of twelve of these subunits (dodecamer or protomer). Each subunit has a molecular weight of between 200 and 250 kDa, and constitutes the functional unit of the native molecule.

Preferably, the extracellular hemoglobin of annelids is chosen from the extracellular hemoglobins of polychaete annelids, preferably from the extracellular hemoglobins of the family Arenicolidae and the extracellular hemoglobins of the family Nereididae. Even more preferentially, the extracellular hemoglobin of annelids is chosen from the extracellular hemoglobin of *Arenicola marina* and the extracellular hemoglobin of Nereis, more preferentially the extracellular hemoglobin of *Arenicola marina*.

According to the invention, the composition may also comprise at least one globin protomer of the extracellular hemoglobin of annelids. Said protomer constitutes the functional unit of native hemoglobin, as indicated above.

Finally, the composition may also comprise at least one globin chain of the extracellular hemoglobin of annelids. Such a globin chain may in particular be chosen from the Ax and/or Bx type globin chains of extracellular hemoglobin of annelids.

The extracellular hemoglobin of annelids and globin protomers thereof have intrinsic superoxides dismutase (SOD) activity, and consequently require no antioxidant in order to function, contrary to the use of a mammalian hemoglobin, for which the antioxidant molecules are contained in the red blood cells and are not bonded to the hemoglobin. Furthermore, the extracellular hemoglobin of annelids, globin protomers thereof and/or globins thereof do not require a cofactor in order to function, contrary to mammalian hemoglobin, in particular human hemoglobin. Finally, the extracellular hemoglobin of annelids, globin protomers thereof and/or globins thereof do not possess blood typing; they make it possible to avoid any problem of immunological reaction.

The composition according to the invention may also comprise a stabilizing solution, the composition of which is compatible with an organ preservation solution. This stabilizing solution creates a saline environment which is suitable for the hemoglobin, protomers thereof and globins thereof, and thus enables the quaternary structure and therefore the functionality of this molecule to be maintained. By virtue of the stabilizing solution, the hemoglobin, protomers thereof and globins thereof are capable of performing their organ oxygenation function.

The stabilizing solution according to the invention is an aqueous solution comprising salts, preferably chloride, sodium, calcium, magnesium and potassium ions, and confers on the composition according to the invention a pH of between 6.5 and 7.6; its formulation is similar to that of a physiologically injectable liquid, and it can be used alone as a preservation solution, or in combination with the hemoglobin, or in combination with a commercial organ-preserving solution. Under these conditions, the extracellular hemoglobin of annelids, globin protomers thereof and globins thereof remain functional, and the composition according to the invention, administered at between 0° C. and 37° C. to the donor, is compatible with the organs to be preserved and to be oxygenated.

In the present description, the pH is understood to be at ambient temperature (25° C.), unless otherwise mentioned.

Preferably, the stabilizing solution is an aqueous solution comprising sodium chloride, calcium chloride, magnesium chloride, potassium chloride, and also sodium gluconate and sodium acetate, and has a pH of between 6.5 and 7.6, preferably equal to 7.1±0.5, preferably of approximately 7.35. More preferentially, the stabilizing solution is an aqueous solution comprising 90 mM of NaCl, 23 mM of Na gluconate, 2.5 mM of $CaCl_2$, 27 mM of Na acetate, 1.5 mM of $MgCl_2$, 5 mM of KCl, and has a pH of 7.1±0.5, and can contain between 0 and 100 mM of antioxidant of ascorbic acid and/or reduced glutathione type. Said solution preferably has an osmolarity of between 300 and 350, and preferentially of 302 mOsmol/l.

Finally, the composition according to the invention may comprise an organ preservation solution. This solution makes it possible to maintain the basal metabolism of the cells constituting the transplant organ. It meets a triple objective: to wash the arterial blood from the transplant organ, to bring the transplant organ homogeneously to the desired preservation temperature, and to protect and prevent damage caused by ischemia and reperfusion and to optimize the resumption of function. The organ preservation solution is therefore clinically acceptable.

The organ preservation solution is an aqueous solution which has a pH of between 6.5 and 7.5, comprising salts, preferably chloride, sulfate, sodium, calcium, magnesium and potassium ions; sugars, preferably mannitol, raffinose, sucrose, glucose, fructose, lactobionate (which is an impermeant), or gluconate; antioxidants, preferably glutathione; active agents, preferably xanthine oxidase inhibitors, such as allopurinol, lactates, amino acids such as histidine, glutamic acid (or glutamate) or tryptophan; and optionally colloids such as hydroxyethyl starch, polyethylene glycol or dextran.

According to one preferred embodiment of the invention, the organ preservation solution is chosen from:

University of Wisconsin (UW or Viaspan®) solution, which has an osmolality of 320 mOsmol/kg and a pH of 7.4, having the following formulation for one liter in water:
Potassium lactobionate: 100 mM
KOH: 100 mM
NaOH: 27 mM
$KH_2PO_4$: 25 mM
$MgSO_4$: 5 mM
Raffinose: 30 mM
Adenosine: 5 mM
Glutathione: 3 mM
Allopurinol: 1 mM
Hydroxyethyl starch: 50 g/l, IGL-1®, which has an osmolality of 320 mOsm/kg and a pH of 7.4, having the following formulation for one liter in water:
NaCl: 125 mM
$KH_2PO_4$: 25 mM
$MgSO_4$: 5 mM
Raffinose: 30 mM
Potassium lactobionate: 100 mM
Glutathione: 3 mM
Allopurinol: 1 mM
Adenosine: 5 mM
Polyethylene glycol (molecular weight: 35 kDa): 1 g/l, Celsior®, which has an osmolality of 320 mOsm/kg and a pH of 7.3, having the following formulation for one liter in water:
Glutathione: 3 mM
Mannitol: 60 mM
Lactobionic acid: 80 mM
Glutamic acid: 20 mM
NaOH: 100 mM
Calcium chloride dihydrate: 0.25 mM
$MgSO_4$: 1.2 mM
KCl: 15 mM
Magnesium chloride hexahydrate: 13 mM
Histidine: 30 mM, SCOT 15 Multi Organes Abdominaux® and SCOT 30 Greffons Vasculaires® from Macopharma, both comprising in particular high-molecular-weight (20 kDa) polyethylene glycol, BMPS Belzer®, or Belzer machine perfusion solution, or KPS1, comprising in particular 100 mEq/l of sodium, 25 mEq/l of potassium, a pH of 7.4 at ambient temperature, and having an osmolarity of 300 mOsm/l, Custodiol® HTK Solution, having the following formulation for one liter in water, the pH being 7.20 at ambient temperature, and the osmolality being 310 mOsm/kg:
NaCl: 18.0 mM
KCl: 15.0 mM
$KH_2PO_4$: 9 mM
Hydrogenated potassium 2-ketoglutarate: 1.0 mM
Magnesium chloride hexahydrate: 4.0 mM
Histidine.$HCl.H_2O$: 18.0 mM
Histidine: 198.0 mM
Tryptophan: 2.0 mM
Mannitol: 30.0 mM
Calcium chloride dihydrate: 0.015 mM, Euro-Collins®, which has an osmolality of 355 mOsm/kg and a pH of 7.0, and having the following formulation for one liter in water:
Sodium: 10 mM
Potassium: 115 mM
Chloride: 15 mM
$H_2PO_4^-$: 15 mM
$HPO_4^{2-}$: 42.5 mM
$HCO_3^-$: 10 mM
Glucose: 194 mM, Soltran®, which has an osmolality of 486 mOsm/kg and a pH of 7.1, and having the following formulation for one liter in water:
Sodium: 84 mM
Potassium: 80 mM
Magnesium: 41 mM
$Sulfate^-$: 41 mM
Mannitol: 33.8 g/l
Citrate: 54 mM
Glucose: 194 mM, Perfadex®, which has an osmolarity of 295 mOsmol/l having the following formulation in water:
50 g/l of dextran 40 (molecular weight: 40 000),
$Na^+$: 138 mM,
$K^+$: 6 mM,
$Mg^{2+}$: 0.8 mM,
$Cl^-$: 142 mM,
$SO_4^{2-}$: 0.8 mM,
$(H_2PO_4^- + HPO_4^{2-})$: 0.8 mM and
Glucose: 5 mM, Ringer Lactate®, having the following formulation in water, the pH being between 6.0 and 7.5 at ambient temperature, and having an osmolarity of 276.8 mOsmol/l:
$Na^+$: 130 mM,
$K^+$: 5.4 mM,
$Ca^{2+}$: 1.8 mM,
$Cl^-$: 111 mM,
Lactates: 27.7 mM,
Plegisol®, having the following formulation in water:
KCl: 1.193 g/l,
$MgCl_2.6H_2O$: 3.253 g/l,
NaCl: 6.43 g/l,
$CaCl_2$: 0.176 g/l,
Solution of the Edouard Henriot hospital, having the following formulation in water, the pH being equal to 7.4 at ambient temperature, and which has an osmolarity of 320 mOsmol/l:
KOH: 25 mM,
NaOH: 125 mM,
$KH_2PO_4$: 25 mM,
$MgCl_2$: 5 mM,
$MgSO_4$: 5 mM,
Raffinose: 30 mM,
Lactobionate: 100 mM,
Glutathione: 3 mM,
Allopurinol: 1 mM,
Adenosine: 5 mM,
Hydroxyethyl starch 50 g/l,
and the Steen® solution, comprising human serum albumin, dextran and extracellular electrolytes with a low potassium concentration.

All these organ preservation solutions are commercial products.

Preferably, the composition according to the invention comprises (i) the stabilizing solution and (ii) the organ preservation solution, preferably one of the commercial solutions described above, in a (i):(ii) weight ratio of between 0:100 and 100:0.

Preferably, the composition according to the invention has a pH of between 6.5 and 7.6, and comprises:
at least one globin, one globin protomer or one extracellular hemoglobin of annelids;
calcium ions, preferably in an amount of between 0 and 0.5 mM;
KOH, preferably in an amount of between 20 and 100 mM;
NaOH, preferably in an amount of between 20 and 125 mM;
$KH_2PO_4$, preferably in an amount of between 20 and 25 mM;
$MgCl_2$, preferably in an amount of between 3 and 5 mM;
at least one sugar chosen from raffinose and glucose, preferably in an amount of between 5 and 200 mM;
adenosine, preferably in an amount of between 3 and 5 mM;
glutathione, preferably in an amount of between 2 and 4 mM;
allopurinol, preferably in an amount of between 0 and 1 mM; and
at least one compound chosen from hydroxyethyl starch, polyethylene glycols of various molecular weights and human serum albumin, preferably in an amount of between 1 and 50 g/l.

Typically, the extracellular hemoglobin of annelids, globin protomers thereof and/or globins thereof is present at a concentration, relative to the final volume of composition, of between 0.001 mg/ml and 100 mg/ml, preferentially between 0.005 mg/ml and 20 mg/ml and more preferentially between 1 mg/ml and 5 mg/ml, in particular 1 mg/ml.

Typically, the composition according to the invention has an osmolarity of between 250 and 350 mOsm/l, preferably between 275 and 310 mOsm/l and preferably of approximately 302 mOsm/l.

Preferably, the composition according to the invention comprises (i) the extracellular hemoglobin of annelids, globin protomers thereof and globins thereof, (ii) the organ preservation solution and (iii) the stabilizing solution, for a hemoglobin dose of between 0 g/l and 150 g/l, for a dilution of the organ preservation solution in a volumetric ratio of $8 \times 10^{-3}$ to 100 percent.

According to one preferred embodiment, the temperature of the compositions according to the invention is between 0° C. and 37° C., preferentially between 2° C. and 32° C., preferentially between 4° C. and 25° C. and more preferentially approximately 4° C.

The compositions according to the invention make it possible to work both under hypothermic conditions and under normothermic conditions (close to physiological temperature).

The subject of the invention is also a method for preserving an organ ex situ in a donation after brain death donor or a donation after cardiac death donor, comprising the following steps:

a) perfusion of said deceased donor with a composition comprising at least one globin, one globin protomer or one extracellular hemoglobin of annelids, a stabilizing solution and/or an organ preservation solution, said composition having a temperature of between 0° C. and 37° C., preferentially between 2° C. and 5° C., more preferentially of approximately 4° C., or with an aqueous solution comprising sodium chloride, calcium chloride, magnesium chloride, potassium chloride, sodium gluconate and sodium acetate, and optionally one or more antioxidants, said aqueous solution having a pH of between 6.5 and 7.6, preferably equal to 7.1±0.5, preferably of approximately 7.35; then b) harvesting of the organ to be transplanted; then c) static or dynamic-perfusion preservation of said organ obtained in b), at a temperature of between 0° C. and 37° C., preferentially between 2° C. and 25° C., more preferentially of approximately 4° C., for a time predetermined according to said organ, in the composition or the aqueous solution defined in step a).

The expression "time predetermined according to said organ" is intended to mean a preservation time which is specific and depends on the organ to be transplanted, as indicated above.

The composition according to the invention is preferably administered by injection, in particular by intravascular injection. It can also be administered by normothermic extracorporeal membrane oxygenation (normothermic ECMO), i.e. with an arterial catheter, a venous catheter and a Fogarty catheter, or by hypothermic extracorporeal membrane oxygenation (hypothermic ECMO) for generalized cooling of the donor. It can also be administered using a double-balloon triple-lumen catheter or any other similar technique.

The normothermic ECMO or hypothermic ECMO system is a technique for extracorporeal circulation of blood fluid.

The double-balloon triple-lumen catheter enables, for its part, in situ cooling of the abdominal organs. In particular, when it is implanted in the femoral arterial circuit, it makes it possible to isolate the renal circulation. A rapid perfusion of the composition according to the invention can be carried out through the double-balloon triple-lumen catheter. A discharge route is implanted in the femoral vein, allowing evacuation of the perfused liquid composition.

The invention is now illustrated by means of the examples below, which are not limiting.

Example 1

Materials and Methods
Production and Use of M101 in Preservation Solutions

M101 (HEMO2Life®, Hemarina SA, France) is a buffered solution of *Arenicola marina* hemoglobin, and was manufactured using standard procedures for the extraction of biological products in accordance with health authority specifications. The purified protein is frozen at −80° C. and then thawed at 4° C. before the experiment and diluted in a preservation solution: UW (ViaSpan®, Bristol Myers Squibb, Belgium), HTK (Custodiol®, Germany), IGL (IGL-1®, Institut Georges Lopez, France), Celsior (Celsior®, Genzyme, France), Ringer Lactate (RL, Aguettant, France) or Perfadex (Perfadex®, Vitrolife, Sweden).

Functional Analyses of M101
Oxygen Fixing

M101 was added (1 g/l) to the UW solution. $N_2$ gas was used to deoxygenate the solution, or else LLC-PK1 cells were incorporated into the preparation, and then the two preparations were hermetically sealed. The functionality of M101 was monitored by spectrophotometry [35], making it possible to characterize the oxyhemoglobin and the deoxyhemoglobin. The absorption spectra were recorded over the range 390-650 nm (UVmc2, Safas, Monaco). Dissolved $O_2$ ($dO_2$) was checked using an $O_2$ sensor (Metler Toledo, France).

SOD Activity

The SOD activity of M101 was evaluated by means of a nitro blue tetrazolium (NBT) assay modified by Oberley and Spitz [36]. Briefly, superoxide was generated by xanthine and xanthine oxydase in the presence of catalase and DETAPAC. Reduction of the NBT was detected by spectrophotometry at 560 nm. KCN was added for 1 h at 4° C. before beginning the experiment in order to deactivate the Cu/Zn-SOD complex. A Cu/Zn-SOD complex derived from bovine erythrocytes was used as a control (Calbiochem). A decrease in absorbance indicates an increase in scavenging activity. The percentage inhibition of superoxide anion production was calculated using the formula: [(A0−A1)/A0× 100], where A0 is the absorbance of the control and A1 is the absorbance of the samples.

Structural Analyses of M101

M101 was added (1 g/l) to solutions, and its structure was monitored over time by isocratic gel filtration at ambient temperature with an automatic sampler fixed at 4° C. using an HPLC system (Dionex, France) and a 1 cm×30 cm Superose 6C column (fraction range 5-5000 kDa, GE Healthcare, France). The flow rate was 0.5 ml/min and the eluate was monitored with a photodiode detector over the range 250-700 nm. The elution curves were acquired and processed using the Chromeleon® software (Dionex).

The dissociation curve was obtained by normalization of the area of the M101 peak at the time t (At) with the area of the M101 peak at the time 0 (At0), and plotted as a function of time. The Prism GraphPad software (GraphPad software, USA) was used to adjust the curve on a linear profile ($f(At/At0)=-kd \cdot t$, $T\ 1/2=1/(2 \cdot kd)$) or a monoexponential profile ($f(At/At0)=a \cdot \exp[-kd \cdot t]$). Acceptability was judged with the best correlation coefficient. The dissociation constant (kd) and the half-life (T½) were deduced from the best adjusted curve: linear or monoexponential.

Experiments on Cells at 4° C.

LLC-PK1 porcine proximal tubule cells (CL-101, ATCC, LGC Standards, France) were cultured as previously described [37]. Cold ischemia lesions were simulated by storing a monolayer of cells at 4° C. under an ambient atmosphere in a preservation solution (UW, HTK, IGL, Celsior, RL or Perfadex) optionally supplemented with M101.

The assays were:
for necrosis: the release of lactate dehydrogenase (LDH) was tested using an in vitro toxicology assay kit;
for apoptosis: caspase-3 activity was determined using the fluorimetric Caspase-3 assay kit (R & D Systems, France);
for viability: the metabolic activity was determined using the MTT test;
for energy content: intracellular ATP was determined using the adenosine 5'-triphosphate (ATP) bioluminescent test kit. The kits were used according to the manufacturer's guidelines. The reactions were quantified with a multilabel reader (Victor 3, Perkin-Elmer, France).

For each parameter, the results are expressed as percentage of the values measured in the cells preserved in the cold relative to the value measured in the cells before the lesion (control).

In Vivo Surgical Procedures and Experimental Groups

Male pigs of Large White type (INRA/GEPA, Surgères, France) were prepared as previously described [4] in accordance with the French recommendations of the Commission d'Ethique pour l'Homme et des Etudes chez l'Animal [Ethics Committee for Human and Animal Studies]. The right kidney was harvested, the cold was injected and maintained for 24 hours before the transplantation; this time was chosen because it is slightly longer than the cold ischemia time gathered by the United Network for Organ Sharing for renal allografts (19.6±8.4 h in 2000 [43]). The left kidney was nephrectomized in order to mimic the kidney mass in a transplanted situation. The surgical teams had no knowledge of which protocol was being used. The time for the vascular anastomoses was 30±5 minutes, the blood loss was minimal and no post-operative complication was observed. Four groups were studied:
1-UW: organ preservation with UW;
2-UW+M101: UW supplemented with 5 g/l of M101;
3-HTK: HTK;
4-HTK+M101: HTK supplemented with 5 g/l of M101.
The controls were animals on which sham operations were performed.

Functional Parameters

The pigs were placed in a metabolic cage for the measurements of diuresis (ml/24 h), of blood creatine levels (mol/l), of excreted sodium fraction (%) and of proteinuria (g/24 h), as described previously [3-5].

Morphological Studies

Biopsies were taken 7 days, 14 days and 1 month after reperfusion. Border loss and endoluminal detachment were evaluated using a 6-point semiquantitative scale: 0—no abnormality; 1—slight lesions affecting less than 25% of the kidney samples; 2—lesions affecting 25-50% of the kidney samples; 3—lesions affecting 51-75% of the kidney samples; 4—lesions affecting more than 75% of the kidney samples and 5—widespread necrosis and renal lesions [38].

The quantitative determination of interstitial invasion was adapted from the Banff classification [39]: 0—no inflammatory mononuclear cells in the tubules; 1—foci with 1 to 4 mononuclear cells per tubule cross section or ten tubule cells; 2—foci with 5 to 10 mononuclear cells per tubule cross section and 3—foci of more than 10 mononuclear cells per tubule cross section. Tubulointerstitial fibrosis was determined using Picrosirius staining [40].

Immunohistochemistry was used to measure the invasion of ED1+ and CD3+ cells (SouthernBiotech, USA). The quantitative evaluation was carried out on the 5-10 high-voltage fields (200×).

Statistical Methods

The mean±SEM or SD is indicated. The in vitro data were compared using Dunnett's test. For the in vivo data the Mann-Whitney U test was used for comparisons between 2 groups (only the comparisons UW compared with UW+M101, and HTK versus HTK+M101, were carried out). Correlations were measured with the Spearman test and the dependence of the effect of M101 on the solution used was tested using an ANOVA test. The SPSS software (IBM, USA) and the Graphpad software (Graphpad, USA) were used for the statistical analyses. Significance was accepted for $p<0.050$.

Results

Functionalities of M101

$O_2$ Binding:

The M101 molecule in solution with UW is deoxygenated by bubbling with $N_2$ or by adding LLC-PK1 cells. The data obtained with the cells give the same results as with $N_2$. Under ambient atmospheric conditions, M101 dissolved in UW is in $HbO_2$ conformation (normoxia). The preparation was then hermetically sealed and the $O_2$ was consumed by the cells (hypoxia). After 75 min of hypoxia, the spectrum of M101 gradually changes to the deoxy-Hb conformation with a shift of the Soret band, a decrease in the Beta and Alpha bands, and an increase in the absorbance around 555 nm (data not shown). Complete deoxygenation occurred after 90 min of hypoxia: the spectrum shows a Soret with a maximum at 428 nm and a plateau with a maximum at 555 nm, that is to say a spectrum characteristic of a deoxy-Hb derivative. This state is reversible, since oxygenation of the preparation brings about a return to the initial spectrum of M101. The measurement of the $dO_2$ correlates with the light absorption spectra (data not shown).

SOD Activity (Data not Shown):

M101 is an effective antioxidant, with total inhibition of NBT formation (93.5±1.1%). This activity relates to Cu/Zn-SOD since KCN, which is a specific inhibitor of the enzymatic activity of Cu/Zn-SOD, totally inhibits the scavenging capacity of M101.

M101 is Stable in the Commercial Preservation Solutions (Data Now Shown)

The stability of M101 was analyzed in UW, HTK, IGL, Celsior, RL and Perfadex. The dissociation constants and half-life of M101 show that it is stable for long periods of time.

M101 Protects Cells In Vitro Against Lesions Caused by Cold Storage (Data not Shown)

Keeping the kidney epithelial cells in the standard solution, UW, was very harmful. The evaluation of cell viability by LDH release demonstrated a loss of viability of the cells after 12 h of CS. No significant activation of caspase-3 was detected. The metabolic activity and the ATP content were reduced concomitantly with the LDH release.

M101 protects against these events: only 0.312 g/l were sufficient to significantly improve the structural and metabolic integrity and the energy content after 24 hours. Total protection was achieved at 1.25 g/l of M101 (LDH release: 6±8%; MTT test: 71±13% and ATP content: 78±23%). The cell energy content is increased with concentrations above 2.5 g/l (ATP content>120% relative to the control). M101 also protected the renal cells in a time-dependent manner: cell integrity is completely preserved (LDH release<20%) for 24 hours at 1.25 g/l, for 36 h at 2.5 g/l, 48 h at 5 g/l and 72 hours at 10 g/l. Experiments were reproduced with other solutions: RL, Perfadex, HTK, IGL and Celsior. As per UW, keeping the cells in these solutions causes structural and/or functional cell damage. Two types of results were obtained: 1) in the same way as for UW, the cells stored cold in RL and, to a lesser extent, in Perfadex, exhibit both structural and functional damage; 2) cells stored cold in HTK, IGL or Celsior exhibit only functional lesions. In each solution, supplementation with M101 protects both the integrity of the cells and the functionality of the cells (LDH release<20% under all the conditions and MTT test: 50-100%).

Recovery of the Renal Function of the Transplant Organ In Vivo More Rapid with M101

The pigs transplanted with a kidney preserved with the UW+M101 mixture recommence urine production on day 1 (compared with day 2 for UW), and had a faster recovery to stable urine production levels on day 4 (data not shown, $p=0.016$). The HTK groups had an equivalent recovery of diuresis. The serum creatinine levels in the UW group showed high levels reaching a peak on day 3, and subsequently a slow decrease. The UW+M101 animals showed significantly lower levels, reaching their peak on day 1, and recovered the pre-transplant levels on day 7 ($p=0.009$ at all times, data not shown). The HTK animals showed a high serum creatinine peak on day 1, followed by a slow recovery above the pre-graft levels, whereas the HTK+M101 animals have a much lower peak on day 1 ($p=0.009$), and a faster recovery to the pre-transplant level on day 11. The sodium reabsorption measurements showed a much higher performance level in the kidneys preserved with M101 compared with the solution alone.

The Tissue Integrity is Preserved Better in the Transplant Organs with M101

The evaluation of the loss of the brush border and of cell detachment, i.e. typical IRI tubule lesions, revealed considerable damage in the UW transplants on days 7 and 14, this stabilizing at month 1. The kidneys preserved in UW+M101 exhibited less widespread lesions. The HTK groups showed a similar tendency toward improvement of the histological lesions using M101.

The Inflammation is Less Severe in the Kidneys with M101

There was considerable immune response involvement in the UW transplants throughout the follow-up. The kidneys preserved in UW+M101 showed little immune infiltration from the beginning, and reduced signs of inflammation subsequently. The two HTK groups showed a low level of infiltration. At 3 months, the invasion of inate (ED1+) and adaptive (CD3+) immune cells reveals a decrease in invasion levels in the kidneys preserved with M101 compared with the solution alone.

Result Improved by Supplementation with M101

The pigs were sacrificed at 3 months, i.e. at the time when the inventors have shown the development of chronic fibrosis in this model [41, 42]. The development of interstitial fibrosis and tubular atrophy (IFTA) in the UW transplant organs was wide spread (23%), whereas supplementation with M101 significantly reduced it (11%, $p=0.049$). The HTK kidneys also showed a considerable IFTA development (25%). Here also, the addition of M101 significantly reduced the development of damage (10%, $p=0.038$).

The histological damage was associated with a chronic loss of function, since the two HTK and UW groups showed high levels of serum creatinine and of proteinuria. For the two solutions, supplementation with M101 significantly reduced these levels.

Supplementation with M101 Correlates with Better Results at the Beginning and after 3 Months Other statistical analyses showed that supplementation with M101 correlated negatively with creatinine levels on day 3 ($R2=0.75$, $p=0.0001$) and with sodium excretion levels on day 3 ($R2=0.74$, $p=0.0001$). In addition, the inventors determined that supplementation with M101 also has a negative correlation with a chronic result (3 months): with creatinine ($R2=0.75$, $p=0.0001$), proteinuria ($R2=0.55$, $p=0.013$) and fibrosis ($R2=0.78$, $p=0.0001$).

The ANOVA revealed that there was an interaction between M101 and the solution used for an acute result: with creatinine blood levels ($p=0.001$) and sodium reabsorption ($p=0.04$) on day 3; whereas the chronic effects of M101 after 3 months are independent of the solution used (data not shown).

REFERENCES

[1] Salahudeen A K. Cold ischemic injury of transplanted kidneys: new insights from experimental studies. American journal of physiology. 2004 August; 287(2):F181-7.

[2] Salahudeen A K. Cold ischemic injury of transplant organs: some new strategies against an old problem. Am J Transplant. 2004 January; 4(1):1.

[3] Faure J P, Baumert H, Han Z, Goujon J M, Favreau F, Dutheil D, et al. Evidence for a protective role of trimetazidine during cold ischemia: targeting inflammation and nephron mass. Biochemical pharmacology. 2003 Dec. 1; 66(11):2241-50.

[4] Hauet T, Goujon J M, Vandewalle A, Baumert H, Lacoste L, Tillement J P, et al. Trimetazidine reduces renal dysfunction by limiting the cold ischemia/reperfusion injury in autotransplanted pig kidneys. J Am Soc Nephrol. 2000 January; 11(1):138-48.

[5] Jayle C, Favreau F, Zhang K, Doucet C, Goujon J M, Hebrard W, et al. Comparison of protective effects of trimetazidine against experimental warm ischemia of different durations: early and long-term effects in a pig kidney model. American journal of physiology. 2007 March; 292(3):F1082-93.

[6] Simmons M N, Schreiber M J, Gill I S. Surgical renal ischemia: a contemporary overview. The Journal of urology. 2008 July; 180(1):19-30.

[7] Kosieradzki M, Rowinski W. Ischemia/reperfusion injury in kidney transplantation: mechanisms and prevention. Transplantation proceedings. 2008 December; 40(10):3279-88.

[8] Favreau F, Thuillier R, Cau J, Milin S, Manguy E, Mauco G, et al. Anti-thrombin therapy during warm ischemia and cold preservation prevents chronic kidney graft fibrosis in a DCD model. Am J Transplant. January; 10(1):30-9.

[9] Giraud S, Thuillier R, Belliard A, Hebrard W, Nadeau C, Milin S, et al. Direct thrombin inhibitor prevents delayed graft function in a porcine model of renal transplantation. Transplantation. 2009 Jun. 15; 87(11):1636-44.

[10] Dragun D, Hoff U, Park J K, Qun Y, Schneider W, Luft F C, et al. Ischemia-reperfusion injury in renal transplantation is independent of the immunologic background. Kidney Int. 2000 November; 58(5):2166-77.

[11] Koo D D, Welsh K I, Roake J A, Morris P J, Fuggle S V. Ischemia/reperfusion injury in human kidney transplantation: an immunohistochemical analysis of changes after reperfusion. The American journal of pathology. 1998 August; 153(2):557-66.

[12] Cassie S, Masterson M F, Polukoshko A, Viskovic M M, Tibbles L A. Ischemia/reperfusion induces the recruitment of leukocytes from whole blood under flow conditions. Free Radic Biol Med. 2004 May 1; 36(9):1102-11.

[13] Belzer F O, Southard J H. Principles of solid-organ preservation by cold storage. Transplantation. 1988 April; 45(4):673-6.

[14] Maathuis M R, Leuvenink H G, Ploeg R J. Perspectives in organ preservation. Transplantation. 2007 May 27; 83(10):1289-98.

[15] Minor T, Sitzia M, Dombrowski F. Kidney transplantation from non-heart-beating donors after oxygenated low-flow machine perfusion preservation with histidine-tryptophan-ketoglutarate solution. Transpl Int. 2005 January; 17(11):707-12.

[16] Matsumoto S, Kuroda Y. Perfluorocarbon for organ preservation before transplantation. Transplantation. 2002 Dec. 27; 74(12):1804-9.

[17] Rousselot M, Delpy E, Drieu La Rochelle C, Lagente V, Pirow R, Rees J F, et al. Arenicola marina extracellular hemoglobin: a new promising blood substitute. Biotechnology journal. 2006 March; 1(3):333-45.

[18] Rousselot M, Le Guen D, Zal F. Novel dissociation mechanism of a polychaetous annelid extracellular haemoglobin. FEBS J. 2006 April; 273(7):1582-96.

[19] Zal F, Green B N, Lallier F H, Vinogradov S N, Toulmond A. Quaternary structure of the extracellular haemoglobin of the lugworm Arenicola marina: a multi-angle-laser-light-scattering and electrospray-ionisation-mass-spectrometry analysis. European journal of biochemistry/FEBS. 1997 Jan. 15; 243(1-2):85-92.

[20] Toulmond A. Blood oxygen transport and metabolism of the confined lugworm Arenicola marina (L.). The Journal of experimental biology. 1975 December; 63(3):647-60.

[21] Toulmond A, Tchernigovtzeff C. Ventilation and respiratory gas exchanges of the lugworm Arenicola marina (L.) as functions of ambient PO2 (20-700 torr). Respiration physiology. 1984 September; 57(3):349-63.

[22] Ahlenstiel T, Burkhardt G, Kohler H, Kuhlmann M K. Improved cold preservation of kidney tubular cells by means of adding bioflavonoids to organ preservation solutions. Transplantation. 2006 Jan. 27; 81(2):231-9.

[23] McCord J M. Oxygen-derived free radicals in postischemic tissue injury. The New England journal of medicine. 1985 Jan. 17; 312(3):159-63.

[24] Chabasse C, Bailly X, Rousselot M, Zal F. The multigenic family of the extracellular hemoglobin from the annelid polychaete Arenicola marina. Comp Biochem Physiol B Biochem Mol Biol. 2006 July; 144(3):319-25.

[25] Royer W E, Jr., Omartian M N, Knapp J E. Low resolution crystal structure of Arenicola erythrocruorin: influence of coiled coils on the architecture of a megadalton respiratory protein. J Mol Biol. 2007 Jan. 5; 365(1):226-36.

[26] Favreau F, Thuillier R, Cau J, Milin S, Manguy E, Mauco G, et al. Anti-thrombin Therapy During Warm Ischemia and Cold Preservation Prevents Chronic Kidney Graft Fibrosis in a DCD Model. Am J Transplant. 2009 Dec. 2.

[27] Bernhardt W M, Gottmann U, Doyon F, Buchholz B, Campean V, Schodel J, et al. Donor treatment with a PHD-inhibitor activating HIFs prevents graft injury and prolongs survival in an allogenic kidney transplant model.

Proceedings of the National Academy of Sciences of the United States of America. 2009 Nov. 23.

[28] Bos E M, Leuvenink H G, Snijder P M, Kloosterhuis N J, Hillebrands J L, Leemans J C, et al. Hydrogen Sulfide-Induced Hypometabolism Prevents Renal Ischemia/Reperfusion Injury. J Am Soc Nephrol. 2009 Jul. 23.

[29] Hosgood S A, Nicholson M L. Hydrogen sulphide ameliorates ischaemia-reperfusion injury in an experimental model of non-heart-beating donor kidney transplantation. The British journal of surgery. 2009 Dec. 23.

[30] Kumar S, Allen D A, Kieswich J E, Patel N S, Harwood S, Mazzon E, et al. Dexamethasone Ameliorates Renal Ischemia-Reperfusion Injury. J Am Soc Nephrol. 2009 Sep. 24.

[31] Yoshida J, Ozaki K S, Nalesnik M A, Ueki S, Castillo-Rama M, Faleo G, et al. Ex vivo Application of Carbon Monoxide in UW Solution Prevents Transplant-Induced Renal Ischemia/Reperfusion Injury in Pigs. Am J Transplant. February 25.

[32] Companiesandmarkets.com. Organ Preservation Solutions—A Global Strategic Business Report. 2010 [cited; Available from: http://www.companiesandmarkets.com/Summary-Market-Reort/organ-preservation-solutions-a-global-strategic-business-report-317184.asp

[33] Pereira-Sampaio M A, Favorito L A, Sampaio F J. Pig kidney: anatomical relationships between the intrarenal arteries and the kidney collecting system. Applied study for urological research and surgical training. The Journal of urology. 2004 November; 172(5 Pt 1):2077-81.

[34] Giraud S, Favreau F, Chatauret N, Thuillier R, Maiga S, Hauet T. Contribution of Large Pig for Renal Ischemia-Reperfusion and Transplantation Studies: The Preclinical Model. Journal of Biomedicine and Biotechnology. in press.

[35] Assendelft, ed. Spectrophotometry of haemoglobin derivatives. Assen, The netherlands: Charles C Thomas Publisher, Royal Vangorcum LTD 1970.

[36] Oberley L W, Spitz D R. Assay of superoxide dismutase activity in tumor tissue. Methods Enzymol. 1984; 105:457-64.

[37] Dutheil D, Rioja-Pastor I, Tallineau C, Goujon J M, Hauet T, Mauco G, et al. Protective effect of PEG 35,000 Da on renal cells: paradoxical activation of JNK signaling pathway during cold storage. Am J Transplant. 2006 July; 6(7):1529-40.

[38] Hauet T, Goujon J M, Baumert H, Petit I, Carretier M, Eugene M, et al. Polyethylene glycol reduces the inflammatory injury due to cold ischemia/reperfusion in autotransplanted pig kidneys. Kidney international. 2002 August; 62(2):654-67.

[39] Solez K, Colvin R B, Racusen L C, Haas M, Sis B, Mengel M, et al. Banff 07 classification of renal allograft pathology: updates and future directions. Am J Transplant. 2008 April; 8(4):753-60.

[40] Grimm P C, Nickerson P, Gough J, McKenna R, Stern E, Jeffery J, et al. Computerized image analysis of Sirius Red-stained renal allograft biopsies as a surrogate marker to predict long-term allograft function. J Am Soc Nephrol. 2003 June; 14(6):1662-8.

[41] Favreau F, Rossard L, Zhang K, Desurmont T, Manguy E, Belliard A, et al. Expression and modulation of translocator protein and its partners by hypoxia reoxygenation or ischemia and reperfusion in porcine renal models. American journal of physiology. 2009 July; 297(1):F177-90.

[42] Thuillier R, Favreau F, Celhay O, Macchi L, Milin S, Hauet T. Thrombin inhibition during kidney ischemia-reperfusion reduces chronic graft inflammation and tubular atrophy. Transplantation. 2010 Sep. 27; 90(6):612-21.

[43] Fotakis G, Timbrell J A. In vitro cytotoxicity assays: comparison of LDH, neutral red, MTT and protein assay in hepatoma cell lines following exposure to cadmium chloride. Toxicol Lett. 2006 Jan. 5; 160(2):171-7.

[44] Gallucci S, Matzinger P. Danger signals: SOS to the immune system. Current opinion in immunology. 2001 February; 13(1):114-9.

[45] El-Zoghby Z M, Stegall M D, Lager D J, Kremers W K, Amer H, Gloor J M, et al. Identifying specific causes of kidney allograft loss. Am J Transplant. 2009 March; 9(3):527-35.

[46] Copeland J W, Beaumont B W, Merrilees M J, Pilmore H L. Epithelial-to-mesenchymal transition of human proximal tubular epithelial cells: effects of rapamycin, mycophenolate, cyclosporin, azathioprine, and methylprednisolone. Transplantation. 2007 Mar. 27; 83(6):809-14.

[47] Nankivell B J, Chapman J R. Chronic allograft nephropathy: current concepts and future directions. Transplantation. 2006 Mar. 15; 81(5):643-54.

[48] t Hart N A, van der Plaats A, Faber A, Leuvenink H G, Olinga P, Wiersema-Buist J, et al. Oxygenation during hypothermic rat liver preservation: an in vitro slice study to demonstrate beneficial or toxic oxygenation effects. Liver Transpl. 2005 November; 11(11):1403-11.

[49] Kuroda Y, Kawamura T, Suzuki Y, Fujiwara H, Yamamoto K, Saitoh Y. A new, simple method for cold storage of the pancreas using perfluorochemical. Transplantation. 1988 September; 46(3):457-60.

[50] Fujino Y, Kuroda Y, Suzuki Y, Fujiwara H, Kawamura T, Morita A, et al. Preservation of canine pancreas for 96 hours by a modified two-layer (UW solution/perfluorochemical) cold storage method. Transplantation. 1991 May; 51(5): 1133-5.

[51] Yoshikawa T, Suzuki Y, Fujino Y, Kakinoki K, Li S, Goto T, et al. Detailed analysis of mucosal restoration of the small intestine after the cavitary two-layer cold storage method. Am J Transplant. 2005 September; 5(9): 2135-42.

[52] Farrar D, Grocott M. Intravenous artificial oxygen carriers. Hosp Med. 2003 June; 64(6):352-6.

[53] Cataldi A. Cell responses to oxidative stressors. Current pharmaceutical design. 16(12): 1387-95.

[54] Hosgood S A, Mohamed I H, Nicholson M L. The two layer method does not improve the preservation of porcine kidneys. Med Sci Monit. 17(1):BR27-33.

[55] Rolles K, Foreman J, Pegg D E. A pilot clinical study of retrograde oxygen persufflation in renal preservation. Transplantation. 1989 August; 48(2):339-42.

[56] Kakehata J, Yamaguchi T, Togashi H, Sakuma I, Otani H, Morimoto Y, et al. Therapeutic Potentials of an Artificial Oxygen-Carrier, Liposome-Encapsulated Hemoglobin, for Ischemia/Reperfusion-Induced Cerebral Dysfunction in Rats. Journal of pharmacological sciences. September 11.

[57] Spahn D R, Kocian R. Artificial O2 carriers: status in 2005. Current pharmaceutical design. 2005; 11(31):4099-114.

[58] Regner K R, Nilakantan V, Ryan R P, Mortensen J, White S M, Shames B D, et al. Protective effect of Lifor solution in experimental renal ischemia-reperfusion injury. The Journal of surgical research. 2010 December; 164(2):e291-7.

[59] Jouan L, Taveau J C, Marco S, Lallier F H, Lamy J N. Occurrence of two architectural types of hexagonal bilayer hemoglobin in annelids: comparison of 3D reconstruction volumes of *Arenicola marina* and *Lumbricus terrestris* hemoglobins. J Mol Biol. 2001 Jan. 26; 305(4): 757-71.
[60] Weber R E, Vinogradov S N. Nonvertebrate hemoglobins: functions and molecular adaptations. Physiol Rev. 2001 April; 81(2):569-628.
[61] Patel S, Spencer C P. Studies on the Haemoglobin of *Arenicola Marina*. Comp Biochem Physiol. 1963 February; 16:65-82.

The invention claimed is:

1. A method for preserving an organ for donation after brain or cardiac death in a donor, the method comprising administering to the donor a composition comprising at least one extracellular hemoglobin of Arenicola *marina*, a stabilizing solution and/or an organ preservation solution, wherein the composition is at a temperature of between 0° C. and 37° C.

2. The method according to claim 1 wherein the stabilizing solution is an aqueous solution comprising salts, and comprises a pH of between 6.5 and 7.6.

3. The method according to claim 2 wherein the solution is an aqueous solution comprising chloride, sodium, calcium, magnesium or potassium ions.

4. The method according to claim 1, wherein the stabilizing solution is an aqueous solution comprising 90 mM of NaCl, 23 mM of Na gluconate, 2.5 mM of CaCl2, 27 mM of Na acetate, 1.5 mM of MgCl2, 5 mM of KCl, and a pH of 7.1±0.5.

5. The method according to claim 1, wherein the organ preservation solution is an aqueous solution having a pH of between 6.5 and 7.5 and comprising salts; sugars; antioxidants; active agents.

6. The method according to claim 5, wherein the solution is an aqueous solution comprising chloride, sulfate, sodium, calcium, magnesium or potassium ions; sugars selected from mannitol, raffinose, sucrase, glucose, fructose, lactobionate and gluconate; glutathione; active agents selected from xanthine oxidase inhibitors, lactates, and amino acids, and optionally colloids selected from hydroxyethyl starch, polyethylene glycol and dextran.

7. The method according to claim 1, wherein the extracellular hemoglobin of Arenicola *marina* is present at a concentration, relative to the final volume of composition, of between 0.001 mg/ml and 100 mg/ml, and in that the composition has an osmolarity of between 250 and 350 mOsm/l.

8. The method according to claim 7, wherein the extracellular hemoglobin of Arenicola *marina* is present at a concentration, relative to the final volume of composition, of between 1 mg/ml and 5 mg/ml, and the composition has an osmolarity of between 275 and 310 mOsm/l.

9. A method for preserving an organ ex situ in a donation after brain death donor or a donation after cardiac death donor, comprising the following steps:
  a) perfusion of said deceased donor with a composition as defined in claim 1; then
  b) harvesting of the organ to be transplanted; then
  c) static or dynamic-perfusion preservation of said organ obtained in b), at a temperature of between 0° C. and 37° C., for a time predetermined according to said organ, in the composition or the aqueous solution defined in step a).

* * * * *